(12) United States Patent
Cortes

(10) Patent No.: US 6,805,701 B1
(45) Date of Patent: Oct. 19, 2004

(54) METHOD OF ENHANCING IMMUNE RESPONSE

(75) Inventor: Marta Cortes, 120 Central Park South, Suite 1G, New York, NY (US) 10019

(73) Assignee: Marta Cortes, New York, NY (US)

(*) Notice: Subject to any disclaimer, the term of this patent is extended or adjusted under 35 U.S.C. 154(b) by 0 days.

(21) Appl. No.: 09/362,231

(22) Filed: Jul. 28, 1999

Related U.S. Application Data

(60) Provisional application No. 60/094,383, filed on Jul. 28, 1998.

(51) Int. Cl.[7] ................................................. A61N 5/00
(52) U.S. Cl. ................................. 607/89; 606/2; 606/3; 128/898
(58) Field of Search ........................... 128/898; 607/88, 607/89, 42; 606/2, 3, 7–16

(56) References Cited

U.S. PATENT DOCUMENTS 5,914,255 A * 6/1999 Grae ........................ 435/173.1

OTHER PUBLICATIONS

*Periodontal Disease and Respiratory Infections*, Winter, 1999; Oral Health Letter School of Dental Medicine, vol. 1, No. 2, pp. 1–3.
*Gum Disease and Heart Attacks A Connection*, Fall, 1998; Oral Health Letter School of Dental Medicine, vol. 1, No. 1, pp. 1–5.
Charles W. Rhodes, DDS; *Highly Focused ALD Conference Breaks All Records*; Spring, 1999; Wavelengths, vol. 7, Issue 1.
Alan J. Goldstein, DMD; *The Concept of Calibration or The Care and Maintenance of Our Ethical Barometers*; Summer, 1998; Wavelengths, vol. 6, Issue 2.
Donald J. Coluzzi, DDS; *FDA Grants Clearance For "Laser Curettage"*; Spring, 1997; Wavelengths, vol. 5, Issue 1.
Alan J. Goldstein, DMD; *To Communicate*; Fall, 1998; Wavelengths, vol. 6, Issue 3.
*Curriculum Guidelines and Standards for Dental Laser Education Undergo Significant Revision*; Winter, 1998; Wavelengths, vol. 6, Issue 4.
Isao Ishikawa and Akira Aoki; *The Role of Laser in Periodontics*; Jan. 5, 1945; pp. 20–22.
Jorge Pinero, DDS; *Nd: YAG–Assisted Periodontal Curettage to Prevent Bacteremia Before Cardiovascular Surgery*; Mar. 1998; Dentistry Today, vol. 17, No. 3.
Jorge Pinero, DDS; *The PPSP\* Procedure: The Pinero Precardiac Surgical Protocol*; Jan., 1999; Dentistry Today, vol. 18, No. 1.
Robert H. Gregg, DDS and Delwin K. McCarthy, DDS; *Laser ENAP for Periodontal Ligament (PDL) Regeneration*; Nov., 1998; Dentistry Today, vol. 17, No. 11.
Robert H. Gregg, DDS and Delwin K. McCarthy, DDS; *Laser ENAP for Periodontal Bone Regeneration*; May, 1998; Dentistry Today, vol. 17, No. 5.
Bonnie Heald; *Zeroing In on Gum Disease*; Insight.
Robert H. Gregg, DDS; *Lasers in General Dentistry*; Laser Dentist.
Robert H. Gregg, DDS; *Dental Laser ENAP*; Laser Dentist.
C. J. Whitters, et al.; *The Bactericidal Activity of Pulsed Nd–YAG Laser Radiation In Vitro*; Oct., 1994; Lasers in Medical Science, pp. 297–302.

\* cited by examiner

*Primary Examiner*—R. Kearney
(74) *Attorney, Agent, or Firm*—Ralph J. Mancini

(57) ABSTRACT

The present invention generally relates to a method for the site specific enhancement of cytokine release (through chemotaxis) namely beta chemokines and enhance healing via an enhanced overall immune response. The site specific enhancement of cytokine release is achieved by initiating an inflamatory response by laser therapy.

14 Claims, No Drawings

METHOD OF ENHANCING IMMUNE RESPONSE

This application claims benefit to provisional application 60/094,383 filed Jul. 28, 1998.

FIELD OF THE INVENTION

The present invention generally relates to a method of enhancing overall immune response in mammals.

BACKGROUND OF THE INVENTION

Attraction of leukocytes to the inflamed area is a known as a host response to infection. This process involves chemokines. Chemokines are small proteins, approximately 60–70 amino acids, containing cysteine residues which form disulfide bonds. Chemokines are chemotactic cytokines that have a special role in the pathophysiology of disease and may have a potential as targets of specific disease therapy.

The inflammatory responses are the result of a complex interplay between a variety of immune and nonimmune cells. The cytokines are the crucial mediators of tissue repair and inflammation. Cytokine is a general term for any non-antibody protein released by immune cells on contact with an antigen or an immune stimulant. They are produced by a wide array of cell types, such as mononuclear phagocyte, lymphocytes, and endothelial cells, and serve as communication signals among immunocompetent cells as well as between immune cells and connective tissue cells. Specifically, cytokines are involved in chemotaxis, adhesion to vascular endothelium, and subsequent transendothelial migration of leukocytes into target tissue; events that are crucial in the development of an inflammatory response. Endothelial cells when activated by the mononuclear cell-derived proinflammatory cytokines, interleukin-1 (IL-1), interleukin -6 (IL-6) and Tumor Necrosis Factor-alpha (TNF-alpha), produce chemotactic cytokines such as IL-8 and express various molecules for leukocytes, thereby facilitating leukocyte extravasation.

Inflammation is the body's response to infection, or injury, so that activated immune cells release chemokines that draw immune cells to the local site. The area becomes red and warm, or inflamed. Lymphocytes are a family of white blood cells, or immune cells, which includes all types of T-cells and B-cells are primary elements of the antibody-mediated immune response; which also release cytokines which help trigger a wider range of cells, including T-cells. All B-cells are lymphocytes. T-cells are the main actors in the cell-mediated immune response; CD4+t cells and CD8+t cells are lymphocytes as are cytoxic t-lymphocytes (CTLs) and so called "Natural Killer" (NK cells); important in HIV infection.

The present invention generally relates to a method for the site specific enhancement of cytokine release (through chemotaxis) namely beta and alpha chemokines and enhance healing via an enhanced overall immune response.

SUMMARY OF THE INVENTION

The present invention generally relates to a method for the site specific enhancement of cytokine release (through chemotaxis) namely beta and alpha chemokines and enhance healing via an enhanced overall immune response. The site specific enhancement of cytokine release is achieved by initiating an inflammatory response by laser therapy.

DETAILED DESCRIPTION OF THE INVENTION

The chemokines are divided into four families according to the position of the cysteine residues. The largest and most investigated of the families are the alpha and beta chemokine which contain four cysteine amino acids. In the alpha family, one amino acid separates the first two cysteine residues (CXC), where as beta-chemokines has the first two cysteine residues next to each other (CC). The alpha chemokines are chemotactle for neutrophils. The beta-chemokines attract monocytes, eosinophile, basophile, and lymphocytes with variable selectivity . Beta Chemokines of the CC subgroup include RANTES, and MCP-1 (monocyte chemoattractant protein) are potent chemoattractant for monocytes also MCP-3 (monocyte cytochemoattractant protein) and EOTAXIN which are potent eosinophil and monocyte chemoattraction.

Inflammation is the body's response to infection or injury, so that activated immune cells release chemokines that draw immune cells to the local site. The area becomes red and warm, or inflamed. Lymphocytes are a family of white blood cells, or immune cells, which includes all types of T-cells and B-cells are primary elements of the antibody-mediated immune response; which also release cytokines which help trigger a wider range of cells, including T-cells. All B-cells are lymphocytes. T-cells are the main actors in the cell-mediated immune response; CD4+t cells and CD8+t cells are lymphocytes as are cytoxic t-lymphocytes (CTLs) and so called "Natural Killer" (NK cells); important in HIV infection.

Macrophages are leukocytes (white blood cells) which are present in all tissues of the body. Macrophages develop from the bone marrow precursors which mature and enter the bloodstream as monocytes. They secrete (cytokines and chemokines ) and response to a wide range of inflammatory mediators. They secrete protease and growth factors which are important in tissue remodeling and wound repair. Human monocytes express the cell surface glycoprotein CD4 and the co-receptor CCR5 and can be infected by the HIV virus which causes AIDS .

The beta chemokines (as with the CXC family (alpha), the N-terminal amino acid precedes the CC residue ) are a critical component of the biological activity and leukocyte selectivity of these configurational changes via the N-terminal acids next to the cysteine residues sulfate bonds. With the N-terminal amino acids a deletion or an addition may reflect a general mechanism that allows local factors to regulate and amplify chemokine activity. Several chemokines undergo N-terminal proteolytic processing after secretion, which alter their activity. Receptor activation is a cascade of cellular activation, including the generation of inositol triphosphate, the release of intracellular calcium, and the activation of protein Kinase C. Chemokine-receptor signaling also activates small guanosine triphosphate-binding proteins of the Ras and Rho families. Rho proteins are involved in cell motility through regulation of actinodependent process such as membrane ruffling, pseudopod formation, and assembly of focal adhesion complexes.

Chemokines are basic proteins, and they bind avidly to negative charges and heparin sulfate. Heparin sulfate proteoglycans capture chemokines in the extracellular and on the surface of endothelial cells, a process that may serve to establish a local concentration gradient from the point of chemokine secretion. It appears, therefore, that the release of the chemokines involve the slicing of the sulfite bond and therefore, configurational changes, resulting in affinity and activity changes.

Since proinflammatory cytokines stimulate secretion of many of the same chemokines, it has found that through initiation of an inflammatory response, a site specific enhancement of cytokine release (through chemotaxis) namely beta and alpha chemokines and can be instigated thereby enhancing healing via an enhanced overall immune response. Thus, the present invention contemplates a means of inducing an inflammatory response sufficient to enhance cytokine release. While many different means of inducing inflammatory response can be employed within the context and scope of the present invention, the present inventor has found that laser therapy provides a safe, convenient and highly efficient manner of initiating inflammatory response while eliminating the bacterial load and allowing the natural immune system to respondLasers are known to be useful in a variety of applications in medicine including surgery and dentistry. In fact, clinical observations have suggested through laser therapy/surgery, that one can see coagulum, fibrin exudate, fibrous tissue formation and bone formation as in gingival regeneration and bone regeneration. In several studies, it has been shown that laser treatment transforms fibroblast to myofibroblast and that histologically, the laser wounds displayed the generation of new muscle fibers and significant myoblast proliferation.

The present invention has taken the known technology further by providing a method of enhancing overall immune response and health by initiating an inflammatory response as a means for the site specific enhancement of cytokine release (through chemotaxis) namely beta chemokines. Chemokines often act in concert with other cytokins to cause tissue infiltration, by increasing the circulating pool of a given leukocytes and an up-regulation of particular adhesion molecules as well as increasing leukocyte responsiveness to a chemokin. For example, eotaxin and interleukin-5 together cause tissue eosinophils, and interleukin-5 and interleukin-3 prime basophils to release histamine and leukotriene after stimulation by monocyte chemoattractant protein.

There have been studies on cytokine release of the low energy laser irradiation using a routine therapeutic laser at clinically relevant energy densities on two different immunocompetent cell types of human origin, i.e. monocytes and endothelial cells, but they were unable to demonstrate a modulatory effect on the release of TNF-alpha, IL-6 and IL-8 by LPS stimulated monocytes at much lower energy densities, similar to those applied clinically. The present inventors have, however, unexpectedly discovered that the use of a higher energy laser with set parameters of, for example, 3–6 watts is effective in initiating inflammatory response thereby enhancing cytokine release and the immune system.

Any laser capable of initiating inflammatory response is useful in the context of the present invention. This includes but is not limited to gas lasers such as helium neon, $CO_2$ argon, krypton, helium-cadium krytton fluoride; solid state lasers such as neodymium yttrium aluminum garnet (Nd: YAG), ruby titanium sapphire; semiconductor lasers such as aluminum gallium arsenide, indium gallium arsenide, aluminum indium gallium phosphide; liquid lasers, chemical lasers, free-electron lasers and the like. Preferred lasers include the $CO_2$ and the Nd:YAG lasers with the Nd:YAG being the most preferred laser.

The chemokines also play a significant role in immune compromised patients. More specifically, scientists now know that HIV needs to open two key holes to gain entry into target cells: CD4 molecule on helper T cells and macrophage is the first key whole and newly discovered chemokine receptors, these called CCR5 (beta chemokine receptor) and CXCR4(also know as fusin-an alpha chemokine receptor), act as second keyholes that allow HIV entry into cells. In a multinational effort, scientists have developed a way to prevent the infection of T-cells and macrophage by HIV in the laboratory. They have designed a modified chemokine that blocks HIV's capacity to bind CCR5, thus preventing HIV infection of cells. The implication of this finding is staggering. It could be possible to block CCR5 receptors at time of initial infection without affecting an individual's immune system. Scientist are at work to try to develop chemokines antagonist for the CXCR4. Once developed, these antagonist might help prevent the rapid disease progression associated with conversion to tropic virus from M-tropic. The principal cofactor for entry mediated by the envelop glycoprotein of primary macrophage-tropic strains of HIV-1 is CC-CKR-5, a receptor for the beta-chemokin RANTES, MIP-1alpha, and MIP-1beta. In addition, it has been noted that the chemokine receptor CKR-5 must be present at the cell surface for infection to occur. Therefore, it is reasonable to assume that if the CKR-5 receptor is already occupied with the beta-chemokines, then the immune system has better time to clear the HIV virus and replication is prevented. This offers a potentially new target for blocking the viral life cycle at the early point before it enters cells.

It is essential to understand the three circles of disease contribution; the environment, the bacteria and the host resistance, in order to fully appreciate that overall health must be approached as a multifactorial approach. Thus, laser therapy in, for instance, periodontal therapy would not only destroy bacteria which patients are already predisposed to the infection, but would block the CCR5 the receptor sites as a of point of entry to those who are vulnerable, prevent virus duplication and boost the over all immune system. This means that when treating the disease state of periodontal disease, abscesses and oral infections in the oral cavity by laser therapy, we are treating more than bacterial contamination and necrotic tissue. The body is responding with an enhanced immune reaction thereby improving the medical state of the patient and contributing to their overall well being.

I claim:

1. A method for enhancing overall immune response in mammals which comprises initiating a site specific inflammatory response sufficient to enhance cytokine release, wherein said inflammatory response is achieved by cold laser therapy, wherein said laser does not induce thermal shock.

2. The method of claim 1 wherein said laser is selected from the group consisting of gas lasers, solid state lasers, semiconductor lasers, liquid lasers, chemical lasers and free-electron lasers.

3. The method of claim 2 wherein said gas laser is selected from the group consisting of helium neon, $CO_2$ argon, krypton and helium-cadium krytton fluoride.

4. The method of claim 2 wherein said solid state laser is selected from the group consisting of neodymium yttrium aluminum garnet (Nd: YAG) and ruby titanium sapphire-semiconductor lasers such as aluminum gallium arsenide, indium gallium arsenide, aluminum indium gallium phosphide; liquid lasers, chemical lasers, free-electron lasers and the like.

5. The method of claim 2 wherein said semiconductor laser is selected from the group consisting of aluminum gallium arsenide, indium gallium arsenide, and aluminum indium gallium phosphide.

6. The method of claim 1 wherein said laser is operated at an energy level of from 3 to 6 watts.

7. A method for treating a disease or infection in mammals which comprises initiating a site specific inflammatory response sufficient to enhance cytokine release, wherein said inflammatory response is achieved by laser therapy wherein said laser does not induce thermal shock, thereby enhancing said mammals overall immune response to said disease.

8. The method of claim 7 wherein said laser is selected from the group consisting of gas lasers, solid state lasers, semiconductor lasers, liquid lasers, chemical lasers and free-electron lasers.

9. The method of claim 8 wherein said gas laser is selected from the group consisting of helium neon, $CO_2$ argon, krypton and helium-cadium krytton fluoride.

10. The method of claim 8 wherein said solid state laser is selected from the group consisting of neodymium yttrium aluminum garnet (Nd: YAG) and ruby titanium sapphire-semiconductor lasers such as aluminum gallium arsenide, indium gallium arsenide, aluminum indium gallium phosphide; liquid lasers, chemical lasers, free-electron lasers and the like.

11. The method of claim 8 wherein said semiconductor laser is selected from the group consisting of aluminum gallium arsenide, indium gallium arsenide, and aluminum indium gallium phosphide.

12. The method of claim 7 wherein said mammal is a human and said disease is selected from the group consisting of a bacterial infection, a viral infection, cancer and combinations thereof.

13. The method of claim 12 wherein said disease selected from the group consisting of aids and cancer.

14. The method of claim 7 wherein said laser is operated at an energy level of from 3 to 6 watts.

* * * * *